United States Patent [19]

Goldsmid

[11] 4,445,367

[45] May 1, 1984

[54] HARDNESS TESTER

[75] Inventor: Hiroshi J. Goldsmid, Epping, Australia

[73] Assignee: Unisearch Limited, Kensington, Australia

[21] Appl. No.: 323,911

[22] Filed: Nov. 23, 1981

[30] Foreign Application Priority Data

Nov. 25, 1980 [AU] Australia .............................. PE6620
May 28, 1981 [AU] Australia .............................. PE9073
Jul. 17, 1981 [AU] Australia .............................. PE9787

[51] Int. Cl.³ .............................................. G01N 3/48
[52] U.S. Cl. .......................................... 73/81; 374/45
[58] Field of Search ................ 73/81, 83; 374/45, 51, 374/53

[56] References Cited

U.S. PATENT DOCUMENTS 2,535,830 12/1950 Beck .................................... 73/81 X
2,924,771 2/1960 Greenberg et al. ............. 374/45 X

FOREIGN PATENT DOCUMENTS

1060211 3/1954 France ..................................... 73/81
232579 12/1968 U.S.S.R. .................................. 73/81

Primary Examiner—Jerry W. Myracle
Attorney, Agent, or Firm—Michael J. Striker

[57] ABSTRACT

A thermal contact resistance having a thermocouple whereby the contact resistance between a probe of the thermocouple and a test material is less dependant on the thermal conductivity of the test material and more dependent on its hardness.

22 Claims, 7 Drawing Figures

HARDNESS TESTER

The present invention relates to a hardness tester and more particularly to a hardness tester employing thermal contact resistance.

Present hardness testing is carried out by applying a predetermined shape of indenter to a surface to be tested under the action of a known force. Thereafter the size of the indentation is measured by, for example, a microscope and such size relates directly to the hardness of the surface based upon a known calibration. This form of testing suffers from difficulties in applying the test as in situ hardness testing of relatively inaccessible components is virtually impossible.

It is an object of the present invention to provide a thermal contact resistance hardness tester. The following description of the present invention will be directed to thermal contact resistance but it will be appreciated that once the necessary considerations have been made its modification to electrical contact resistance means is apparent.

The hardness tester of the present invention as it relates to a thermal contact resistance device derived from the thermal comparator of the invention as disclosed in co-pending Australian patent application No. 56439/80 the disclosure of which is incorporated herein by reference. In that device the thermal contact resistance between the probe head is made sensitive to the thermal conductivity of the test material by making the thermal conductivity of the probe head relatively high. In addition, in use, the contact area between the probe head and the test materials is kept constant by ensuring that the test material is harder than the probe head.

When two solids are pressed together, the thermal contact resistance is given by $(1/\lambda_1 + 1/\lambda_2)/4r$, where $\lambda_1$ and $\lambda_2$ are the thermal conductivities of the two materials and r is the effective radius of contact (Clark and Powell 1962, Measurement of thermal conduction by the thermal comparator, J. Sci Instrum., 39, 545–51). If the contact radius can be kept constant, the thermal resistance then depends primarily on the lower of the conductivities $\lambda_1$ and $\lambda_2$. This fact has been utilised in a recently developed thermal comparator for testing gemstones, Australian Patent Application 56439/80. In that device, a heated probe (e.g. a copper probe) is pressed against the gemstone using a fixed force. As the probe is softer than a gemstone the effective radius of contact is always the same. Also, since the probe is such a good conductor of heat, it is generally the thermal conductivity of the gemstone that predominates in the expression for the contact resistance.

In a first form the present invention consists in a thermal contact resistance hardness tester comprising a probe head of a relatively hard material so that the thermal contact resistance therebetween relates to the hardness of the test material. It will now be appreciated that a relatively hard probe brought into contact with the test materials under a substantially constant force is required for accurate results.

In a further form the present invention provides a hardness tester for which there is no need to know the thermal conductivity $\lambda_2$ of the test material. This device employs two probes that are brought down together on the specimen. The probes are identical except that one has a relatively soft tip that is pressed against the sample with a small fixed force, while the other has a hard tip which can be applied with a variable load. The two tips should have the same thermal conductivity or, failing this, conductivities that are very much higher than that of any test sample. Any difference between the contact resistances is then due to differences in the effective radii of contact. By varying the load the effective contact radii can be made the same and this can be readily detected.

The present invention aims to make the contact resistance less dependent on the thermal conductivity of the test material and, through changes in the effective radius, more dependent on its hardness. Ideally, in the first form of the invention the thermal conductivity of the probe tip should be significantly lower, and the hardness of the tip significantly higher, than that of the material being tested. The length of the diagonal of the indentation made by a hard pyramidal tool under a given load (or rather its reciprocal) is a commonly employed measure of hardness. It is expected that the effective radius of thermal contact will also be characteristic of the hardness of the material being tested, although there may well be a complex relationship between the two measurements.

In principle, it might seem that one should select a probe tip of the smallest possible thermal conductivity, but this would make the thermal contact resistance very large and heat transfer through the surrounding air would then predominate. Thus it is most advantageous to make the thermal conductivity of the tip only somewhat smaller than that of the test substance. In experiments synthetic ruby has been used for the probe tip; approximate values for the thermal conductivity of ruby and of the materials tested are given in Table 1. Some materials actually have a conductivity less than that of ruby.

TABLE 1
Thermal conductivities near room temperature*

| Material | Thermal conductivity $\lambda_2$ (Wm$^{-1}$ K$^{-1}$) | # $1 + \lambda_1/\lambda_2$ |
|---|---|---|
| Copper | 401 | 1.09 |
| Aluminium | 237 | 1.15 |
| Tungsten | 173 | 1.20 |
| Molybdenum | 138 | 1.25 |
| Brass | 120 | 1.29 |
| Zinc | 116 | 1.30 |
| Chromium | 94 | 1.37 |
| Indium | 82 | 1.43 |
| Iron | 80 | 1.44 |
| Tin | 67 | 1.52 |
| Tantalum | 57 | 1.61 |
| Mild Steel (0.2% C.) | 50 | 1.70 |
| Tool Steel (1.3% C, 0.3% Mn) | 40 | 1.75 |
| Zirconium | 23 | 2.52 |
| Titanium | 22 | 2.59 |
| Stainless steel (304/316) | 17 | 3.06 |
| Yttrium | 17 | 3.06 |

*Typical values from CRC Handbook of Chemistry and Physics, 57th Edn. 1976-7.
Using $\lambda_1$ for ruby equal to 35 W m$^{-1}$ K$^{-1}$.

The present invention will now be described by way of example with reference to the accompanying drawings, in which.

Figure 1:
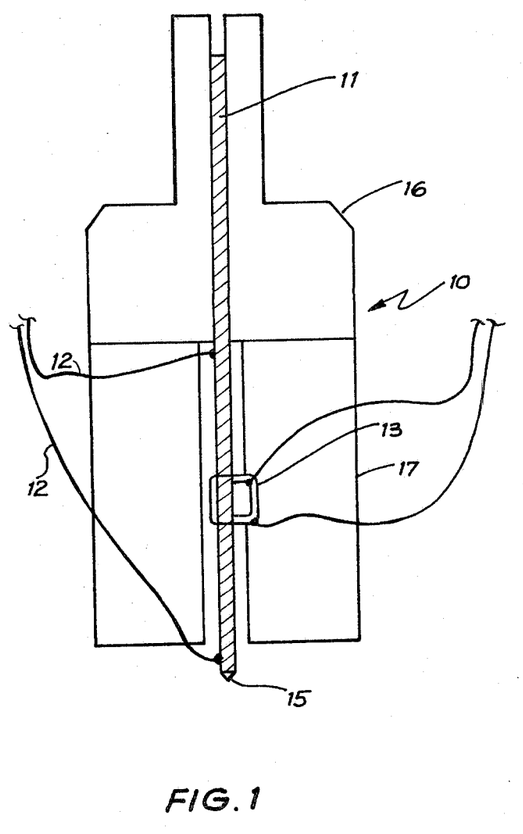
FIG. 1 is a schematic representation of a probe in accordance with the present invention.

Referring to FIG. 1 there is shown a probe 10 designed so as to fit in place of the usual diamond-pyramid head in a Zwick indenter which was also employed (with its diamond head) to determine the hardness by conventional means. The probe 10 consists of a thermocouple made from constantan wire 11 of 1.25 mm diameter with two copper wires 12 of 0.35 mm diameter attached at a spacing of about 10 mm. A 10Ω resistive heater 13 of 2 mm length and 0.8 mm diameter was attached by Araldite resin 14 near the centre of the constantan branch of the couple. The power supplied to the heater was 0.4 watts. The ruby tip 15 was conical, of about 50° half-angle, and its flat base was cemented to the flat end of the constantan wire using E-solder No. 3021, a silver-loaded epoxy adhesive. The free end of the constantan wire was mounted in perspex 16 while the heated region was encased in foamed polystyrene 17 to reduce thermal losses.

Figure 2:
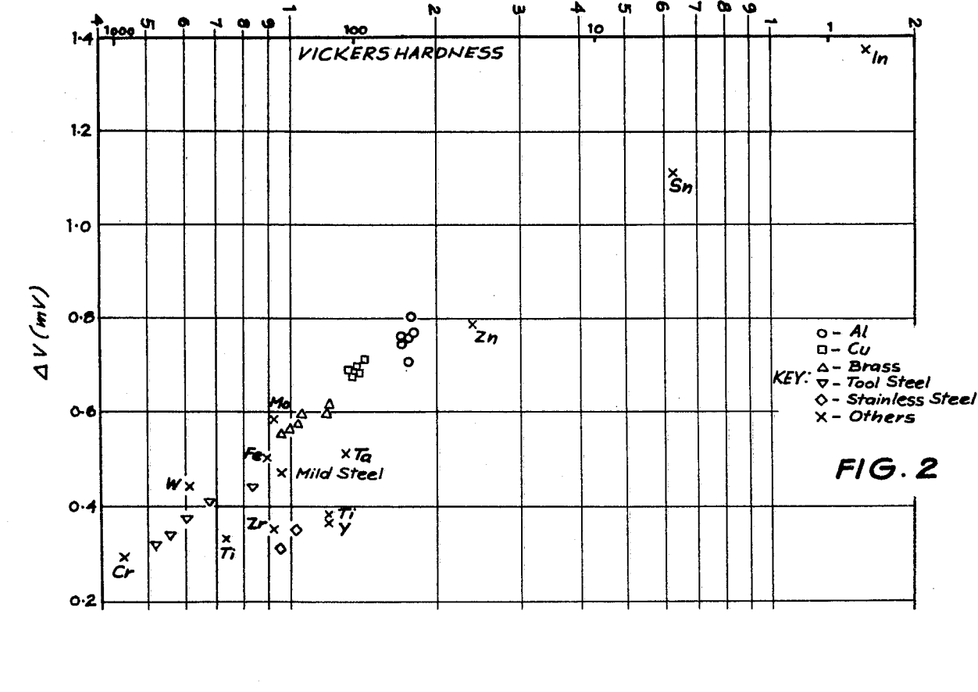
FIG. 2 is a plot of voltage difference as against Vickers hardness on a linear-log graph for a variety of metals.
Figure 3:
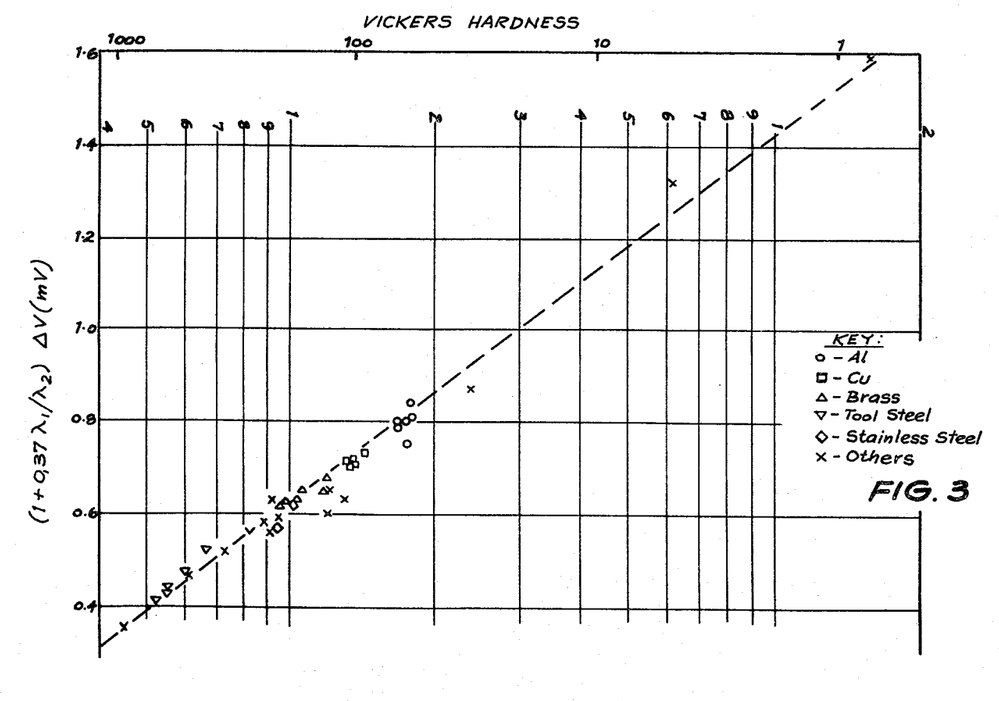
FIG. 3 is a plot of corrected voltage difference against Vickers hardness for the results of FIG. 2.

Before each measurement the thermocouple output was allowed to reach its equilibrium value in air. The probe was then pressed against the test material using a load of 0.3 kg and the maximum e.m.f. from the thermocouple (reached after about a quarter of a minute) was noted. The differnce $\Delta V$ between this maximum e.m.f. and the value before contact was made was then plotted against the length d of the diagonal of the indentation produced by the diamond head with a load of 1.0 kg. The results are shown in FIG. 2. It can be seen that there is a clear tendency for $\Delta V$ to rise with the diagonal length but a number of e.m.f. values fall significantly below the rest. Without exception, these are values obtained for materials of thermal conductivity that is similar to or lower than that of ruby. As shown in the last column of Table 1 $(1+\lambda_1/\lambda_2)$ becomes significantly greater than unity in such cases. Here the subscripts 1 and 2 refer to the ruby and the test material respectively. It is clearly inappropriate to multiply the observed value of $\Delta V$ by $(1+\lambda_1/\lambda_2)$ since as previously shown, part of the heat is lost from the tip around the solid-state interface. Thus it seems appropriate that a correction factor $(1+k\lambda_1/\lambda_2)$ should be applied, where k lies between zero and unity. The results for the stainless steel samples suggest that k should be about 0.37. In FIG. 3 $(1+0.37\lambda_1/\lambda_2) \Delta V$ is plotted against d and it can be seen that the results now all lie close to a single line (that the line is straight on a linear-log plot is fortuitous).

For most metals the thermal conductivity is much greater than that of the probe tip so the correction factor $(1+k\lambda/\lambda_2)$ is not often much larger than unity. A precise value of the thermal conductivity $\lambda_2$ is, thus, not generally needed and a good enough figure may be obtained using a simple thermal comparator of the type used for testing gemstones as discussed in Australian Patent Application No. 56439/80 with, perhaps, the tip made from tin. This would allow thermal conductivity measurements to be made on soft as well as hard materials.

Figure 4:
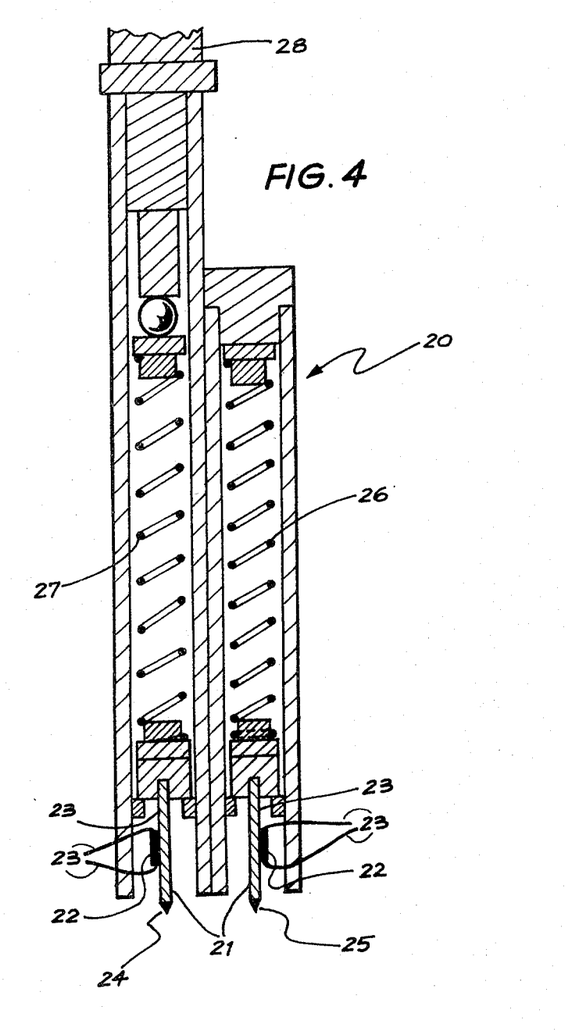
FIG. 4 is a sectional view of a double probe for hardness testing in accordance with the present invention.

A double-probe 20 in accordance with the invention is illustrated in FIG. 4. The common features of the probes are constantan rods 21, of 20 mm length and 1.25 mm diameter, with miniature 12 resistive heaters 22, of 2.0 mm length and 0.8 mm diameter, cemented near their mid-points with Araldite. Copper wires 23 of 0.15 mm diameter are soldered to the resistors 22 and to each end of the constantan rods 21. The tips, which are conical having a 50° half-angle, are made from diamond 24 and copper, 25, respectively, both of which have exceptionally high thermal conductivities. The fact that the thermal conductivity of diamond is typically twice that of copper does not matter provided that the specimen under test does not have too high a conductivity. For example, most steels have thermal conductivities of about 50 W m$^{-1}$ K$^{-1}$, which is an order of magnitude down on the value of copper. The tips are bonded to the ends of the constantan rods with Araldite which although being a substance of low thermal conductivity, does not present any appreciable extra thermal resistance because of its relatively large cross-sectional area.

The copper-tipped probe contains a relatively weak spring 26 that exerts a force of 0.7 N when the tip is retracted by pressing against a flat surface. The force on the diamond tip can be varied between 0 and 20 N by compression of a stiffer spring 27 by means of a micrometer screw 28.

Figure 5:
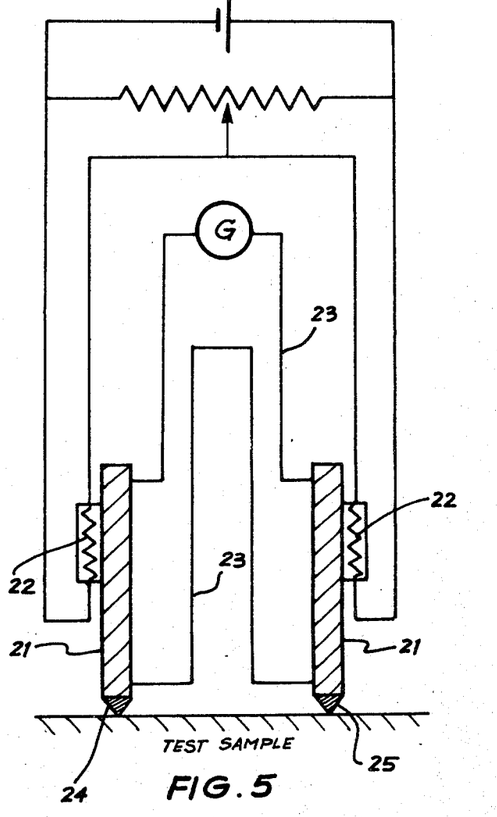
FIG. 5 is an electrical circuit diagram of the probe of FIG. 4.
Figure 6:
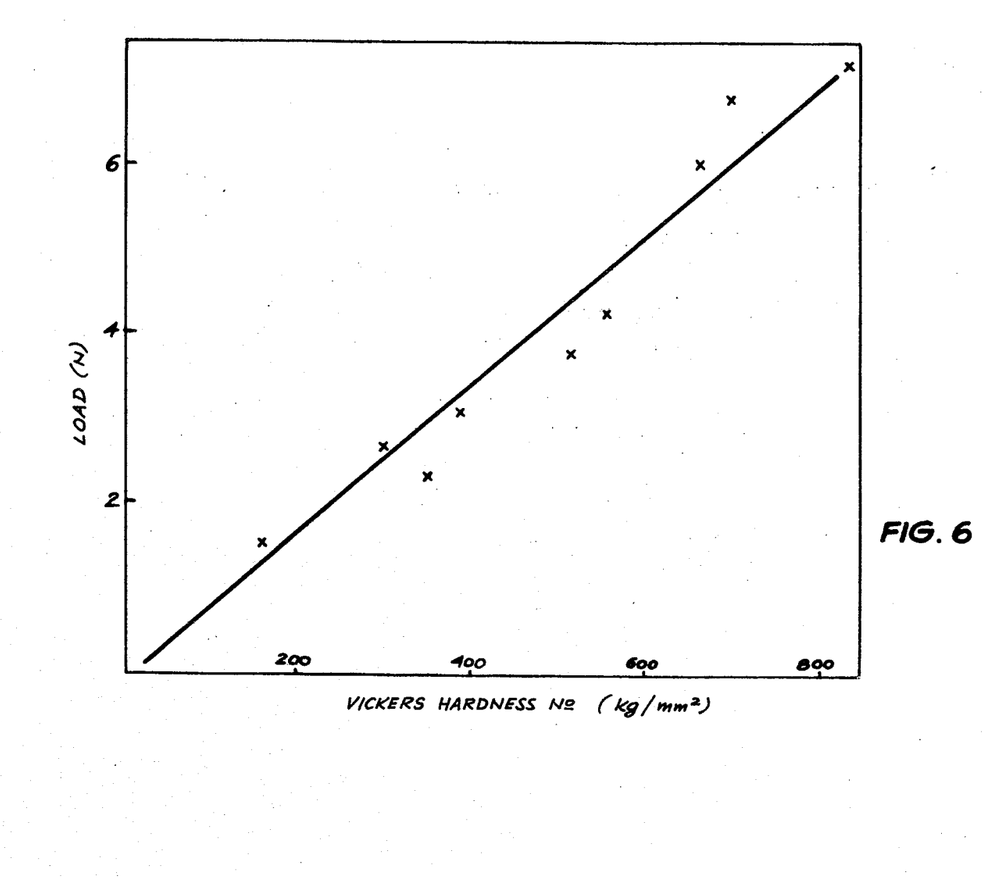
FIG. 6 is a plot of balancing load on diamond probe against Vickers hardness number for a range of steel samples for the tester of FIG. 4.

The constantan rods 21 and their copper leads 23 constitute thermocouples that are connected in opposition as shown in FIG. 5. If the same power is supplied to each heater, then there is zero output to the galvanometer 28 when the thermal resistances at both tips are the same. The 25Ω potentiometer across the 4.5 V supply is used in balancing the power supplied to the heaters 22 which, of course, are only nominally of equal resistance. This balancing is accomplished by equalising the loads on the two tips when applying the double-probe to a soft material (a bar of lead-tin solder was used for this purpose). When the double-probe is then brought down on a test sample (that must be significantly harder than copper) balance between the thermocouple outputs is again obtained by increasing the load on the hard tip. This condition is indicated by a null measurement from the two thermocouples connected in opposition. As we have seen, the effective radius of contact is then always the same and the load to achieve this condition is a measure of the required hardness.

This instrument has been tested using a range of polished steel specimens of high homogeneity having Vickers hardness numbers in the range 152 to 839 kg mm$^{-2}$. The micrometer screw was advanced from the zero position at 10 mm per minute, corresponding to an increase of load at the rate of 8 N per minute, until the balance condition was reached. FIG. 3 shows a typical plot of a single set of load readings against hardness number, as determined with a Vickers diamond indenter.

Figure 7:
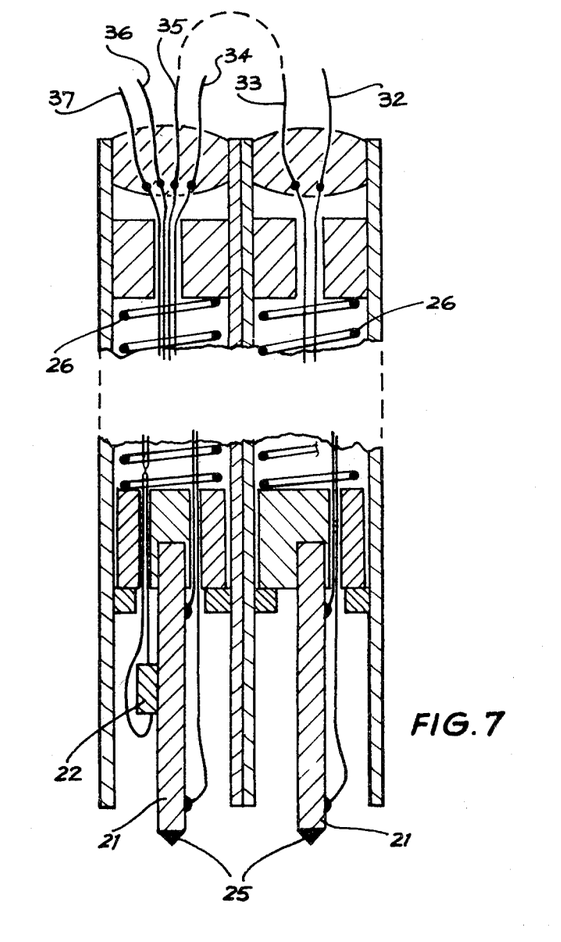
FIG. 7 is a further embodiment of a double probe hardness tester in accordance with the present invention.

The hardness tester 20 of FIG. 7 is formed by two probes joined together in similar manner to that shown in FIG. 4 and wherein like parts are denoted by corresponding numerals. In this embodiment each tip 25 is of the same material and is formed of, say, ruby. Constantan rods 21 are biased by springs 26 which each provide a common force when tips 25 are pressed against a flat specimen up to the limit of retraction of the tips 25 flush with the lowermost extremity 30 of tubes 31. Only one thermocouple is supplied with a resistive heater 22. Wires 32 and 33 lead respectively to the tip and base ends of the unheated rod so as to form a thermocouple. In a similar way wires 34 and 35 form a thermocouple with a heated rod. Wires 36 and 37 are the leads to the resistive heater 22 that is cemented with Araldite near the centre of the left hand rod, the resistor being connected to a regulated voltage source. Wires 33 and 35 are connected together so that the output from wires 32 and 34 become the sum of the e.m.f.'s from the "hot" and "cold" probes; this sum is independent of any difference in temperature that might exist between the sample and its surroundings. The tester 20 of FIG. 7 is particularly suited for use where a material under test is not at ambient temperature.

Use of a hardness tester in accordance with the present invention enables rapid non-destructive means for determining the local hardness of materials.

I claim:

1. A thermal contact resistance hardness tester comprising a probe head of a relatively hard material so that the thermal contact resistance therebetween relates to the hardness of the test material; means for supplying thermal energy to said probe head.

2. A hardness tester as claimed in claim 1 comprising means for providing a substantially constant force between the probe and a test material when said probe is applied to said test material.

3. A hardness tester as claimed in claim 1 or 2 wherein the probe tip has a thermal conductivity slightly lower than that of a material to be tested.

4. A hardness tester as claimed in claim 1 wherein said probe head is attached adjacent a junction between two branches of a thermocouple.

5. A hardness tester as claimed in claim 4 comprising heating means for heating a branch of said thermocouple.

6. A hardness tester as claimed in claim 5 wherein said heating means comprises an electrical resistance heating element.

7. A hardness tester as claimed in claim 1 comprising another probe head of a relatively soft material and wherein the probe heads have substantially the same thermal conductivity or are substantially higher than that of a test material.

8. A hardness tester as claimed in claim 7 comprising means for applying a small constant force via said softer probe to said test material and a variable load via said hard probe to said test material.

9. A hardness tester as claimed in claim 1 comprising another probe head of the same material or of a material having substantially the same hardness and thermal conductivity as said first mentioned probe head.

10. A hardness tester as claimed in claim 7 or 9 wherein said two probes are positioned side by side so that they are brought down together to contact said test material.

11. A hardness tester as claimed in claim 7 or 9 wherein each probe head is attached adjacent a junction between two branches of a respective thermocouple.

12. A hardness tester as claimed in claim 11 comprising heating means for heating a branch of one of said thermocouples.

13. A hardness tester as claimed in claim 12 wherein said heating means comprises an electrical resistance heating element attached to a thermocouple branch.

14. A hardness tester as claimed in claim 11 comprising heating means for heating a branch of each thermocouple.

15. A hardness tester as claimed in claim 14 wherein each heating means comprises an electrical resistance heating element attached to a thermocouple branch.

16. A thermal contact resistance hardness tester comprising a probe head of a relatively hard material so that the thermal contact resistance between the head and a test material relates to the hardness of the test material, means for supplying thermal energy to said probe head; and means for measuring the thermal contact resistance between the probe head and the test material.

17. A hardness tester as claimed in claim 16 wherein the means for measuring the thermal contact resistance comprises a thermocouple and wherein said probe head is attached adjacent a junction between two branches of said thermocouple.

18. A hardness tester as claimed in claim 17 further comprising another probe head of a relatively soft material and wherein the probe heads have substantially the same thermal conductivity or are substantially higher than that of a test material.

19. A hardness tester as claimed in claim 18 wherein each probe head is attached adjacent a junction between two branches of a respective thermocouple of the means for measuring the thermal contact resistance.

20. A hardness tester as claimed in claim 19 wherein said means for supplying thermal energy comprise heating means for heating a branch of one of said thermocouple.

21. A hardness tester as claimed in claim 19 wherein said means for supplying thermal energy comprise heating means for heating a branch of each thermocouple.

22. A hardness tester as claimed in claim 16 wherein said means for supplying thermal energy to said head comprises heating means for heating a branch of said thermocouple.

* * * * *